United States Patent
Moore (10) Patent No.: US 9,655,951 B2
(45) Date of Patent: *May 23, 2017

(54) PRESERVATION OF THE BIOLOGICAL ACTIVITY OF UNDENATURED TYPE II COLLAGEN

(71) Applicant: Eugene R. Moore, Midland, MI (US)

(72) Inventor: Eugene R. Moore, Midland, MI (US)

(73) Assignee: CARTILAST II LLC

( * ) Notice: Subject to any disclaimer, the term of this patent is extended or adjusted under 35 U.S.C. 154(b) by 297 days.

This patent is subject to a terminal disclaimer.

(21) Appl. No.: 13/999,661

(22) Filed: Mar. 14, 2014

(65) Prior Publication Data

US 2015/0017129 A1 Jan. 15, 2015

Related U.S. Application Data

(63) Continuation-in-part of application No. 13/694,971, filed on Jan. 23, 2013, now Pat. No. 9,023,416.

(51) Int. Cl.

| | |
|---|---|
| *A23L 1/315* | (2006.01) |
| *A61K 38/39* | (2006.01) |
| *A23B 4/06* | (2006.01) |
| *A23B 4/09* | (2006.01) |
| *A23B 4/24* | (2006.01) |
| *A23K 20/147* | (2016.01) |
| *A23L 29/281* | (2016.01) |

(Continued)

(52) U.S. Cl.
CPC ............ *A61K 38/39* (2013.01); *A23B 4/066* (2013.01); *A23B 4/09* (2013.01); *A23B 4/24* (2013.01); *A23K 20/147* (2016.05); *A23L 29/284* (2016.08); *A23L 33/17* (2016.08); *A23V 2002/00* (2013.01); *A61K 35/35* (2013.01)

(58) Field of Classification Search
USPC .......................................................... 435/325
See application file for complete search history.

(56) References Cited

U.S. PATENT DOCUMENTS

| | | | | |
|---|---|---|---|---|
| 4,405,490 A | * | 9/1983 | Maas ................. | B01D 19/0404 |
| | | | | 516/117 |
| 2006/0204663 A1 | * | 9/2006 | Nojo ........................ | B41M 5/52 |
| | | | | 427/356 |

(Continued)

*Primary Examiner* — Sharmila G. Landau
*Assistant Examiner* — Stephanie McNeil
(74) *Attorney, Agent, or Firm* — Timothy S. Stevens (57) ABSTRACT

The present invention is the storage of biologically active natural ingredients in carbonated water. In a specific embodiment, the present invention is the storage in carbonated water of animal tissue containing type II collagen. Such type II collagen is useful for alleviating the symptoms of arthritis in mammals as well as the treatment of arthritis in mammals. Such type II collagen is also useful for the prevention of arthritis in mammals. The present invention is also a method for the preparation of a nutritional supplement that includes the steps of: (a) separating animal tissue containing water-insoluble, undenatured type II collagen from animal tissue not containing type II collagen; (b) subdividing and sterilizing said tissue under conditions which do not change the original structure of the type II collagen to produce a subdivided and sterilized product; (c) packaging the subdivided and sterilized product in carbonated water.

1 Claim, 1 Drawing Sheet

(51) Int. Cl.
*A23L 33/17* (2016.01)
*A61K 35/35* (2015.01)

(56) References Cited

U.S. PATENT DOCUMENTS

2007/0249054 A1* 10/2007 Doi .................... C12Q 1/22
 436/15
2010/0196486 A1* 8/2010 Hiraoka ................ A61K 9/10
 424/489

* cited by examiner

PRESERVATION OF THE BIOLOGICAL ACTIVITY OF UNDENATURED TYPE II COLLAGEN

This application is a continuation-in-part of U.S. patent application Ser. No. 13/694,971 filed Jan. 23, 2013 which is a continuation-in-part of U.S. Provisional Patent Application Ser. No. 61/632,645 filed Jan. 27, 2012. Among other things, the invention provides a technique for storing and shipping therapeutic amounts of animal tissue containing a therapeutic amount of undenatured type II collagen and an improved method of preparing and maintaining such collagen in a pure, useful, and undenatured state so it can be consumed and utilized for ameliorating the effects of autoimmune arthritis in warm-blooded mammals, including equine such as horses, donkeys and mules; canines such as dogs and wolves; and humans.

BACKGROUND OF THE INVENTION

Arthritis is a painful and often crippling disease that initially results in painful, swollen, and inflamed joints. It often progresses to deform or completely destroy joints that then require replacement. This disease is a result of the body mistakenly attacking type II collagen, which is the major structural component of cartilage tissue. One function of cartilage tissue is that it serves as a lubricant in the joints, keeping bone from rubbing on bone. As the disease progresses and more of the cartilage is destroyed, bone does begin to wear on bone. The two most prominent types of arthritis are rheumatoid arthritis and osteoarthritis. The usefulness of undenatured type II collagen has been shown in ameliorating the symptoms of osteoarthritis in humans (*Int. J. Med. Sci.*, 6(6), 2009, 312-321), horses (*J. Vet. Pharmacol. Ther.*, 32, 2009, 577-584), and dogs (*J. Vet. Pharmacol. Ther.*, 28, 2006, 385-390), which are all here fully incorporated by reference.

In order to initiate rheumatoid arthritis, it appears that an individual must have an inherent susceptibility. There is now evidence that, in susceptible people, this disease is initiated by exposure to the relatively common Epstein-Barr virus. The ability of the Epstein-Barr virus to initiate rheumatoid arthritis has been linked to a key amino acid sequence which is identical to a sequence found in human type II collagen. Thus, in generating antibodies to destroy the Epstein-Barr virus, the body generates antibodies that are also capable of attacking its own collagen.

Osteoarthritis has recently been found to also be an attack by the autoimmune system on cartilage. It is interesting that osteoarthritis occurs in animal species that do not, as a species, have rheumatoid arthritis. These species include canine, such as dogs, and equine, such as horses. Osteoarthritis is strongly related to age in both animals and humans. One likely reason for this age-related effect is an alternate method for the autoimmune system to be activated to initiate an attack on the body's cartilage. Such activation method may involve the very life-sustaining act of metabolism. In order to convert carbon-based food into $CO_2$ and energy, the body creates massive numbers (many millions) of reactive oxygen species (ROS). In this process of breaking down food and producing energy, DNA chain breakage or other damage is said to occur over a million times per day in the average person. A large portion of this damage relates to cleavage of DNA, which is quickly repaired or destroyed by the immune system. This very routine action of the body's immune system is absolutely vital to human life. Some of the damaged molecules have the potential to cause the immune system to generate antibodies that are then capable of attacking the body's own collagen. When a body ages, a combination of effects causes it to become more susceptible to this osteoarthritis inducement. In some cases the DNA damage repair system becomes weaker. In other cases there may simply be a gradual build up and accumulation of the water-soluble molecular fragments that have the potential to generate antibodies that are capable of attacking the body's own collagen. When a sufficient accumulation of these water-soluble molecular fragments occurs, the collagen-destroying antibodies are activated.

In order to study the effect of proposed techniques for amelioration of arthritis, it is necessary to have arthritic animals. Two techniques to artificially induce arthritis in rats have been developed. These inducements have been accomplished more quickly than for osteoarthritis in humans, but in a similar manner. With rats the newer technique is by intradermal (under the skin) injection of a broken-down, water-soluble fragment of undenatured type II collagen (extracted from chicken cartilage). This technique has been termed collagen-induced arthritis (CIA). The second and older technique is accomplished by intradermal injection of the well-known *Microbacterium tuberculosis* (MT).

It has also been shown that rats can be prevented from getting arthritis via inducement or the effects of inducement can be greatly reduced. This prevention is accomplished by ingestion (or arterial injection) of the same broken-down, water-soluble, difficult-to-prepare fragment of type II collagen for several days prior to the attempted inducement. Once arthritis has been induced, the effects of the disease can be reduced by the continual oral administration of the same broken-down, water-soluble fragment of type II collagen. In later clinical studies with humans having arthritis, oral administration of the broken-down, water-soluble fragment of type II collagen was is shown to be similarly beneficial in reducing the effects of the disease.

Oral administration of this broken-down, water-soluble, undenatured fragment of type II collagen represents the very first technique for amelioration of the symptoms of arthritis offering a reversal rather than simply a slowing of the progress of the disease. This oral technique is believed to effectively reverse the debilitating effects of arthritis by causing desensitization to type II collagen. After this desensitization the body slows or stops the production of antibodies that destroy its own collagen. This process has been called "oral tolerization", which is a partially understood process that the body uses to stop a person's immune system from treating food as a hostile foreign body. If foreign proteins are introduced via the digestive system, the body automatically suppresses the immune system responses to these proteins. It is a technique that has been used in the past to ameliorate simple allergies, such as an allergic reaction to poison ivy or pollen.

Although this oral administration of broken-down, water-soluble, undenatured fragments of type II collagen represents a long-sought and highly desired technique for amelioration of the symptoms of arthritis, the broken-down, water-soluble fragments of type II collagen are difficult to prepare. Typically the fragments are extracted from the tiny sternal cartilages of 2.5-week-old chicks. In a preparation of this prior art, eighty animals were required to produce 19 g of cleaned sterile cartilage dissected free of surrounding tissue. It is typical of the prior art to perform up to seven operations, consisting of extractions or digestions, on each batch of tissue in order to obtain the broken-down, water-soluble fragment of type II collagen. The procedure of this prior art is thus seen to have several serious deficiencies. An extremely large number of animals is required to obtain a small amount of the desired product. The purification procedure is very time-consuming, requiring multiple extractions, digestions, and precipitations. Sometimes ultrafiltration of the final product is required as a final step to remove pathogens from the water-soluble product.

It was later discovered by Dr. Eugene Moore that it is not necessary to break the undenatured type II collagen into a water-soluble state to obtain the full antiarthritic effect when ingested. In U.S. Pat. Nos. 5,645,581; 5,637,321; 5,529,786; and 5,750,144 (which are hereby fully incorporated by reference) Moore surprisingly found that the normal digestive process is sufficient. That is, when the whole, undenatured cartilage is digested, the effective amino acid sequence is separated and passed into the blood stream where it can reduce the symptoms of arthritis. This accomplishes the same goal as the earlier experiments with rats where the desired effect was is obtained by direct injections of the water-soluble fragment into the blood stream. This 26 amino acid sequence has been identified and is presented by Trentham in U.S. Pat. No. 5,399,347 (which is hereby incorporated in full by reference). It was is shown that this sequence, though difficult to prepare from sequencing monomeric amino acids, has amelioration effects for arthritis.

In the above-referenced Moore patents it was is found preferable to utilize the much larger cartilage from young 4- to 6- or more month-old chickens. Such usage made makes more cartilage available that is also easier to maintain in a sanitary state. Although chicken cartilage is preferred, the above-referenced Moore patents teach that cartilage from other animal tissue containing type II collagen can be effectively utilized. Bovine or porcine cartilage, or vitreous humor of eyes, for example, can be used if desired, although solid cartilage is preferred and chicken sternal cartilage is most preferred. Moore's technique for preparation of cartilage for oral administration to humans consists of first dissecting the cartilage free of most or all surrounding tissues so that the cartilage can be, for example, diced into smaller pieces. The diced cartilage is then sterilized by means known in the art and, for example, formed into capsules containing therapeutic levels of type II collagen, said levels being at least about 0.01 gram and preferably from about 0.1 to about 0.5 gram of cartilage to provide a therapeutic dose. The use of more mature chickens in the Moore approach is surprising in view of the prior art which teaches only the use of chicks of less than 3 weeks of age. The usefulness of the more mature chickens allows an almost 100-fold increase in the amount of harvestable cartilage from a single animal. This, of course, makes the desired product more readily available in therapeutic quantities, and also greatly decreases the possibility of micro-contamination due to the reduced handling during separation from relatively fewer animals.

It is difficult to preserve cartilage in its native undenatured state and thus maintain its effectiveness in alleviating the symptoms of autoimmune diseases. In the past, it has been possible to preserve the cartilage by two techniques. For the first technique, the above-referenced Moore patents teach that the collagen can be preserved successfully for an extended period by cleansing, cooling, and storing the cartilage at very low temperatures. Cartilage stored in this manner does not experience the growth of harmful pathogens or change in structure of the collagen which would cause it to become denatured and thus lose its effectiveness. The cleansing state of this process is by sterilization using, for example, chlorine-producing agents and/or hydrogen peroxide. The second technique, shown in the work of Schilling et al. (U.S. Pat. No. 7,083,820 (which is hereby fully incorporated herein by reference) involves drying cleansed cartilage under special low-temperature conditions in the presence of an inorganic salt, which greatly extends the storage life of the collagen Schilling emphasizes the need for stable long-term storage for this cartilage in order to make its beneficial effects available to a wide range of the world's population. He points out the failing of all other known stabilization and storage methods in the following quotation from his patent. "Thus irradiation, thermal processing, the use of preservatives, freeze drying and other known methods of sterilization, are either ineffective or difficult to use to stabilize a product for human consumption which retains the original biologic structure of naturally occurring materials. Accordingly, there is an acute need for a novel method to retain the biologically active component in natural materials in its original form that can be delivered in a safe and cost-effective manner for human consumption and use by other life forms." Schilling further points out the need for maintaining the biological stability for greater than 3 years in the following quotation. "Another major feature of this invention is that the resulting product maintains its microbial safety for greater than 3 years at room temperature storage conditions."

During cleaning and preparation for use, the cartilage is difficult to completely free from biological contamination such as pathogens and other microbes, which is required to maintain its safety. These pathogens and other microbes must be removed to render the undenatured type II collagen fit for human or animal consumption, even after extensive storage. It is desired to have the cartilage free of additives and easy to handle, store, ship, and consume.

The use of carbon dioxide ($CO_2$) gas to inhibit the growth of microorganisms and extend the storage life of fruits, vegetables, meats, and other short-term consumable food items is well known. This knowledge goes back to the time of the Romans who would pack caves with fruit to let the off-gasses due to ripening, largely $CO_2$, accumulate and slow the ripening and thus prolong the eatable quality of the food. This extension in usefulness of the produce is sometimes measured in hours in the case of cut fruit, for example. Such extension in useful life is often measured in days for items such as meat and poultry. The inhibition in ripening for uncut apples and other thickly skinned whole fruits is often measured in weeks as has been shown, for example, by Daniels (*J. Food Prot.*, 48 (6), 1985, 537-537, which is hereby fully incorporated by reference). Daniels also summarizes the use of $CO_2$ as a means to merely retard the deterioration and spoilage of butchered meat or otherwise comminuted food types and thus increase, in a small way, the useful storage life.

Brecht (*Food Tech.*, 34, 1980, 45-50), in another summary of the use of controlled atmosphere to retard spoilage of produce, cites some negative results on the use of gas phase $CO_2$. Brecht reports acetaldehyde accumulation and ultra-structure alterations as examples that suggest that gas phase $CO_2$ induces an uncontrolled breakdown of tissue. The product of the present invention surprisingly does not have these negative results.

Ogilvy (*Food Tech.*, 5, 1951, 97-102) examines the effects of $CO_2$ on prolonging the storage life of cut-up chicken. He uses the concentration of slime-forming bacteria reaching a count of $2 \times 10^8$ per square centimeter as an end of useful life. Ogilvy also notes a common, serious problem when $CO_2$ is used to store meat or fish: discoloration, with an undesired dark brown color developing in poultry flesh. The product of the present invention is surprisingly void of such discoloration at even the highest $CO_2$ levels. The product of the present invention is very white or clear unless purposefully colored with an added dye or other coloring material. Ansuetto et al. (paper presented at Institute of Food Technologists Annual Meeting, Anaheim Calif.; Jun. 10-13, 1984) examines strawberries, along with other produce. He cites data showing that strawberries are particularly susceptible to decay. He extends storage from less than 3 days to about 6 days using a 30% $CO_2$ atmosphere in the packages. He also discusses some cases where higher levels of $CO_2$ are harmful, where berries must be shipped with "scrubbers" such as lime to absorb the otherwise harmful levels of $CO_2$.

SUMMARY OF THE INVENTION

The present invention solves the above-mentioned problems and comprises the discovery of new applications for the use of $CO_2$ provided the $CO_2$ is dissolved in an "aqueous medium" (defined herein as a liquid medium comprising water, preferably more than 50% water by weight, more preferably more than 75% water by weight and yet more preferably more than 90% water by weight). The present invention completely eliminates the requirement to add up to 40 to 60% or more of a salt to the cartilage. In the preferred practice of the present invention, the need for the long, low-temperature drying step is eliminated. The present invention further provides a safe method of storing the cartilage (or other biologically active tissue). The product of the present invention can be packaged so that a consumer can easily vary a dose size to find a preferred dose and repeat that dose. We have surprisingly found that, when properly prepared cartilage is stored in carbonated water, the storage life of such cartilage is measured in years and such storage life appears to be unlimited. Prior art of $CO_2$ storage to preserve food value gives no indication of long-term storage or maintaining effectiveness in ameliorating the effect of arthritis after long-term storage.

The liquid product packaging of the present invention offers advantages over the dry product of the '820 patent. These advantages come from the potential to be manufactured, wholesaled, distributed, and consumed by those that have experience with, or a preference for, a liquid product. A particular advantage is the ability of a liquid product to be promoted by existing distributors that promote liquid-packaged products. Liquid products can also be placed into retail locations that are relatively convenient and selectively attractive to thirsty potential consumers. Any company that manufactures, wholesales, distributes, or retails any sports drink, health-promoting drink, or joint-health-promoting drink might take advantage of their experience with liquid product or the experience of those in their existing supply chain. Liquid-packaged product offers the advantage of being located with bottled soda and/or liquid health-promoting drinks. For example, liquid product appears behind glass doors or refrigerators near cash registers located in grocery stores or health clubs. Distinct and convenient point-of-sale retail locations allow a consumer to read labels while waiting in line, become informed of the product, and see product which might otherwise only be seen elsewhere at the retail location in more obscure places.

More specifically, in one embodiment the present invention is a method for storing, in an aqueous medium, tissue containing type II collagen, comprising the step of surrounding the tissue with the aqueous medium, the aqueous medium containing more than 0.01% $CO_2$ by weight. In another embodiment, the present invention is a method for alleviating the symptoms of arthritis in mammals comprising the following steps: (a) orally administering a composition obtained by separating animal tissue containing water-insoluble, undenatured type II collagen from animal tissue not containing type II collagen, (b) subdividing and sterilizing said tissue under conditions which do not change the original structure of the type II collagen to produce a subdivided and sterilized product, (c) storing the subdivided and sterilized product in an aqueous medium containing more than 0.01% $CO_2$ by weight to produce the composition, which composition is administered in an amount effective and for a time effective to alleviate such symptoms.

In yet another embodiment, the present invention is a process for the treatment of arthritis in mammals which consists of the steps of: (a) removing, under sterile conditions, tissue containing mostly type II collagen to produce a sterile tissue; (b) storing the sterile tissue in an aqueous medium containing more than 0.01% $CO_2$ by weight to produce a stored sterile tissue; and (c) orally ingesting therapeutic quantities of said stored sterile tissue. In still yet another embodiment, the present invention is a method for the prevention of arthritis in mammals comprising the steps of: (a) removing, under sterile conditions, tissue containing type II collagen to produce a sterile tissue; (b) storing the sterile tissue in an aqueous medium containing more than 0.01% $CO_2$ by weight to produce a stored sterile tissue; and (c) orally ingesting a quantity of said stored sterile tissue sufficient to prevent arthritis in the mammal. In another embodiment, the present invention is a method for the preparation of a nutritional supplement, comprising the steps of: (a) separating water-insoluble undenatured type II collagen containing animal tissue from most or all animal tissue not containing type II collagen; (b) subdividing and sterilizing said tissue under conditions which do not change the original structure of the type II collagen to produce a subdivided and sterilized product; (c) packaging the subdivided and sterilized product in an aqueous medium containing more than 0.01% $CO_2$ by weight. In a yet further embodiment, the present invention is a method for freezing animal tissue containing undenatured type II collagen by the step of cooling the tissue at a rate sufficiently slow so that the type II collagen essentially remains in the undenatured state. Freezing is often desired for shipping to a distant processing station. This would be useful for consumers requiring particular food preparation customs such as halal or kosher.

The process of the present invention also relates to the improved utility of a wide variety of naturally occurring substances of known beneficial effect which retain the original natural structure of such substances while eliminating microbial agents that can affect their quality and efficacy. Another major feature of the present invention is that the resulting product maintains its microbial safety for as much as 9 years or more at room-temperature storage conditions. In addition, any deleterious enzyme activity is controlled, resulting in a more desirable, commercially attractive product since enzymatic activity can bring about negative organoleptic properties, such as inappropriate odors. In addition, enzymatic activity can negatively affect the efficacy of a natural product. The process of the present invention also provides an improved, economical method of converting naturally occurring substances to stable, consumable products that can also be used with other products, which heretofore have been treated with such things as chemical preservatives, thermal processing, irradiation, and other antimicrobial stabilization methods.

DETAILED DESCRIPTION OF THE INVENTION

The process of this invention comprises the use of aqueous $CO_2$ for the safe storage of type II collagen while maintaining the biological activity of this cartilage tissue (or other tissue containing type II collagen). The process effectively eliminates the growth of trace pathogens as well as microbes that might cause spoilage. More specifically, the process of the present invention involves storing said cartilage for relatively long periods of time in the presence of aqueous $CO_2$, preferably after treating with antimicrobial agents. The pH of the aqueous medium of the present invention is preferably less than 7. Preferably, no oxygen is added to the aqueous medium of the present invention. Said storage conditions, in addition to eliminating any remaining traces of pathogens and microbes that might cause spoilage, are shown to surprisingly keep the cartilage in its unaltered, undenatured, and thus most effective state.

There are a large number of naturally occurring substances that have found applications in various fields that must be processed to be suitable as commercial products. Historically, maintaining the biological activity of certain potentially useful substances along with presenting this to the intended recipient in a safe manner, particularly regarding pathogen safety and the control of deleterious enzyme activity, is costly and frequently results in a decrease of the efficacy as a result of denaturing of the biologically active material. There are several commercial fields that market products based on naturally occurring biologically active products, such as pharmaceutical and dietary supplements, food products, medical products, over-the-counter medicines, and cosmetics. The process of the present invention can be adapted to uses in all of these fields. The recent introduction of the dietary supplement business, where small amounts of material are allowed to be consumed, gives particular meaning to this invention. Not only are the products resulting from the process of the present invention stable and consumable for long periods; in addition, naturally occurring substances retain their natural original structure and thus complete efficacy contained in such substances. As a result, improved products are obtained that are useful as dietary supplements, pharmaceuticals, over-the-counter medicines, topical creams or lotions (such as a biologically active cream), and special ingredients in functional foods. The process of the present invention is preferably used with proteins that have shown promise and usefulness as food supplements or pharmaceuticals when the original structure of the protein has not been denatured and the desirable synergism resulting from the interaction of the various protein species found in natural proteins has been protected.

One example of an application of the process of this invention is in the preparation of type II collagen intended for arthritis sufferers. This compound is reported to work with the arthritis sufferer's immune system in a positive manner. As disclosed in the aforementioned Moore patents (U.S. Pat. Nos. 5,570,144; 5,529,786; 5,637,321; and 5,645,851), it is clear that for the type II collagen to be most effective it must be prepared in a manner that is closest to its native state. In these patents, Moore's suggested delivery of this material to the consumer, however, involves the retention of significant amounts of water, thus making the product susceptible to pathogen cross-contamination.

In the over-the-counter medicine field, willow bark was first chewed to lower fever and reduce pain as early as 400 BC, as suggested by Hippocrates. Because of a number of problems in making the product widely available, including storing, handling, and distributing the product, a chemist working in Germany in 1898, Felix Hoffman, synthesized and stabilized the active ingredient in willow bark, acetylsalicylic acid, known today as aspirin. The present invention, when applied to the storage and shipping of willow bark, produces a stable material that can be more effective than synthesized aspirin. In the food product field, a margarine-like spread is now available in supermarket dairy cases that contains plant sterol esters. These esters, derived from oilseed production, have been shown to reduce cholesterol. The process of this invention can be used to stabilize oilseed in a manner that makes it safe, effective, and easier to consume. Oilseed can show reduced efficacy when treated in established ways to reduce enzymatic degradation. In the pharmaceutical field, digitalis is a drug used to create a more effective heartbeat. Digitalis is a glycoside obtained from common foxglove leaves, classified as *Digitalis purpurea*. The process of the present invention can be used to stabilize foxglove leaves in a manner that is safer and more effective and more affordable for the consumer. In the medical field, type I, III, and IV collagens are known to be beneficial for skin health and are used to help wound healing. The process of the present invention can be used to stabilize these collagens in a biologically active and safe form for use in wound healing while making the product more affordable to the consumer. In the cosmetic field, many facial skin creams contain collagen. The process of the present invention can be used to stabilize these collagens in a biologically more active and safe form.

Thus, irradiation, thermal processing, use of preservatives, and other known methods of sterilization are either ineffective or difficult to use to stabilize a product for human or other mammal use or consumption, retaining the original biologic structure of naturally occurring materials. Accordingly, there is an acute need for the present invention to retain the biologically active component in natural materials in its original form that can be delivered in a safe and cost-effective manner for use by humans and other mammals.

Among other things, this invention provides a technique for storing and shipping naturally occurring organic materials which contain a biologically active component, and in particular proteins, that essentially does not change the original structure of the active component. Many other naturally occurring organic materials which contain a biologically active component are also included in the scope of this invention. This invention provides a method for storing and shipping a wide variety of materials which contain a biologically active component that essentially does not change the original structure of the active component. Among other things, this invention provides a new and novel technique for storing and shipping therapeutic amounts of animal tissue containing a therapeutic amount of undenatured type II collagen, and a new and improved method of preparing and maintaining such collagen in a pure, useful, and undenatured state so it can be consumed and utilized for ameliorating the effects of autoimmune arthritis in warm-blooded mammals, including equine such as horses, donkeys, and mules; canine, such as dogs and wolves; and humans. The principle objective of this invention is directed toward type II collagen. Many forms of arthritis are identified as autoimmune arthritis which includes both rheumatoid arthritis and osteoarthritis. It should be understood that throughout this disclosure the terms "rheumatoid arthritis and osteoarthritis" are used interchangeably in reference to an attack by the immune system on the type II collagen contained in joint cartilage, the effect which is reduced in a significant amount or even prevented by the present invention.

In some cases it is more convenient in the process of the present invention, such as for ease of grinding, to produce a product that can be dried and ground in a pathogen-killing atmosphere, then resuspended in aqueous $CO_2$ for long-term storage, shipping, and consumption. In another embodiment of this invention we show that even with the disadvantage of long, low-temperature drying requirements it is possible to produce a dried product that is more concentrated, yet does not require the 40 to 60% dilution with an inorganic salt as required by Schilling. By aseptically packaging this material made according to this embodiment of the present invention, it is found that a highly desired product is produced that in pill or capsule form can be about half of the size of the Schilling product or the same size with double the active ingredient. It is worth noting that effective storage times of more than 8 years are observed in the present invention. The availability of long storage times without loss of biological activity allows time for storing, shipping, displaying, and all of the activities absolutely necessary to successfully deliver an effective product to ameliorate the symptoms of those suffering from the effects of autoimmune arthritis. It was recently reported in Consumer Reports (February 2014, 30-36, hereby incorporated by reference) that commercial chicken usually contains harmful bacteria that must be destroyed by thorough cooking. They report, for example, that: "97 percent of the breasts we tested harbored bacteria that could make you sick." This is evidence of the antimicrobial challenge facing the art. In a later example it will be shown that the slight short-term extended storage of fresh, bacteria-containing chicken treated according to Ogilvy is different from the requirements of retaining the desired arthritis ameliorating activity. While Schilling does achieve long-term "shelf" stability, his procedure has the disadvantage of requiring a long, low-temperature drying step and near 50% dilution with an inorganic salt. Since pill or capsule size is very important in the ability to swallow, the larger pill size required to accommodate about 50% salt diluent is a disadvantage.

The minimum concentration of the $CO_2$ in the aqueous medium of the present invention is about 100 parts per million (ppm) by weight. More preferably, the concentration of $CO_2$ used in the present invention is 1,000 ppm or more by weight. Most preferably, the concentration of $CO_2$ used in the present invention is 3,000 ppm or more by weight. As storage pressure is increased, the $CO_2$ content of the aqueous medium is increased. The upper limit of $CO_2$ appears to only be limited by the pressure limit of the desired storage vessel, or pressure at which, upon opening the vessel, the product of the present invention is expelled in an unacceptable manner. When water is used in the present invention it is preferable that the water be a pH 7 or less, supersaturated with $CO_2$, and stored in a sealed pressure-resistant container.

As disclosed in the four previously mentioned patents of Dr. Eugene Moore, the use of undenatured type II collagen reduces the symptoms of rheumatoid arthritis. As mentioned above, a recent clinical trial (*Int. J. Med. Sci.*, 6(6), 2009, 312-321) has also shown effectiveness of undenatured cartilage against osteoarthritis. Osteoarthritis combined with rheumatoid arthritis presents a very serious health problem affecting a large portion of the world's aging population.

In a preferred practice of this invention, after first removing most or all visible physical contaminants, an antimicrobial agent is used to remove most pathogens or microbes that might cause spoilage. Antimicrobial agents such as sulfur dioxide, ethylene oxide, chlorine, sodium hypochlorite (NaOCl), or a source of active oxygen such as hydrogen peroxide ($H_2O_2$) are useful to carry out this sterilization function. Carefully controlled x-rays or the like may in some cases be useful and desired. This treatment might involve x-rays, gamma rays, electron beams, or ultraviolet (UV) light. Preferably the sterilization agent is chlorine, NaOCl, or a source of active oxygen such as $H_2O_2$. It is important to control the dose so that most pathogens are destroyed without significantly denaturing the collagen. This sterilization function may be carried out initially as well as during processing. The idea is to have most or preferably all of these pathogens and antimicrobial agents removed or destroyed before storage in a $CO_2$-containing medium, thereby lengthening the safe storage period. When carbonated water is used, a visual observation of the stored product is one indicator of undesirable growth of pathogens or other microbial agents. In this case haze or cloudiness is one indicator of growth while another indicator is discoloration. Therapeutic levels of type II collagen in the present invention are at least about 0.01 gram per day and preferably from about 0.1 to about 0.5 gram per day.

It is desired that the pathogens and microbes be greatly reduced by the above sterilization type pretreatment. If such pretreatment is not carried out, storage time of the cartilage is significantly shortened. Successful or useful storage time, however, for this untreated cartilage is lengthened by increasing the $CO_2$ concentration in the liquid. The increase in storage time, however, is not enough to meet the commercial requirements of several years, emphasizing the need to greatly reduce or completely remove the pathogens and microbes by the above sterilization type pretreatment in the preferred embodiment of the present invention.

Figure 1:
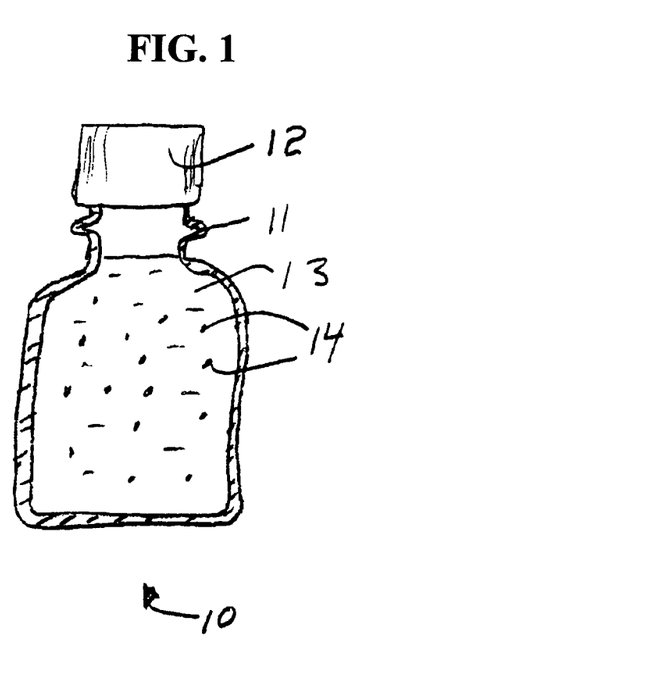
FIG. 1 is a side view, part in full and part in cross-section, of a suspension in carbonated water of cartilage particles containing type II collagen.

While special vessels capable of higher pressure can easily be obtained to package and ship cartilage in bulk where desired, it is generally preferred to package and ship in readily available containers and bottles that are already designed for the moderate pressures required for commercial carbonated beverages, such as soft drinks, vitamin or mineral drinks, and the like. Plastic bottles, such as those produced from polyethylene terephthalate (PET), are preferred for medium-term storage, or for longer term storage when thin nonpermeable coatings are applied internally. Surprisingly, single- or multiple-dose packaging in thinner, plastic, bubble-like containers using low-permeability plastics such as vinyl chloride/vinylidene chloride copolymers are operable. Multiple-dose packaging in larger, self-metering, plastic bottles is in some cases desirable. Glass bottles are preferred for longest term storage. The lower permeability of glass allows for almost perfect retention of $CO_2$. However, glass-lined plastic bottles (such as plastic bottles the interior of which is coated with a thin glass-like layer by a plasma vapor deposition process) are also preferred in the present invention because such containers are shatter resistant and have greatly reduced permeability. Referring now to FIG. 1, therein is shown a preferred embodiment 10 of the present invention wherein a glass bottle 11 having screw cap 12 contains a suspension in carbonated water 13 of cartilage particles 14 containing type II collagen.

After the cartilage is free of most or all of the surrounding flesh and preferably treated with one or more antimicrobial agents, it can be placed into the aqueous $CO_2$ environment. If the cartilage is from the chicken sternum, the pieces are small enough to even be stored whole in small, readily available containers. If the cartilage is from larger animals such as cows or pigs, special containers may be required to store the cartilage in its original physical shape. Cartilage from chicken sternum is most readily available and is generally preferred, for this and other reasons. Usually chicken sternum cartilage, as received from chicken processing facilities, contains 10% by weight or more of attached flesh. It is desired, in most cases, to remove this attached flesh. However, we have noted that the use of $H_2O_2$ in a final treatment process removes all discoloration and yields a very pleasing, all-white suspension. Removal of this flesh by hand is labor-intensive. We have discovered that mechanical abrasion with materials such as common grains or wood pellets can remove most of the attached flesh. Although there are many approaches to applying this abrasion, we have found that a rotating tumbler or an oscillating container works well. In some cases it is desirable to slow freeze and then abrade at low temperatures. When whole cartilage is used it can easily be separated from the smaller abrasive material by common mechanical techniques such as screening. It is preferred to have the abrasive material be combustible. In this combustible case, the abrasive material containing the removed flesh may be dried after separation, if necessary, and used for fuel. In addition to capturing fuel value, a waste disposal problem is avoided.

In most cases it is desired to reduce the size of the original cartilage particles by any one of the many techniques known to those familiar with the art of size reduction. This technique can involve slicing equipment that would use sharp blades. This slicing may be carried out by hand with razor blades, or with stamping equipment using a matrix of blades, or preferably in an aqueous medium containing $CO_2$ using a rotating blade such as that found in a common food blender. An antifoam agent, such as a silicone resin dispersion or other agents familiar to those in the antifoam art, may be used to reduce foam breaking time. In some cases it is useful to individually package a large section of cartilage or a collection of smaller cartilage particles equivalent to the desired therapeutic dose. This may be accomplished by hand or by automatic weighing equipment. Surface water may be removed before weighing by a variety of techniques, such as centrifuging or blotting. To obtain much finer particles, particles of various sizes can be combined, then passed through an elongated orifice under very high pressure. The high shear field developed causes further size reduction. Pressures across a single orifice can be as high as 5,000 to 10,000 psig. A series of progressively smaller orifices allows for progressively smaller particle sizes. We have found that the collagen in the vitreous humor of bovine eyes, for example, is particularly useful when comminuted in this manner. Smaller particles can be produced using lower shear fields. This may be due to the type II collagen being so uniformly dispersed and low in concentration. Such size reduction is limited, in the extreme, by loss of effectiveness as the key 26 amino acid sequence begins to show significant breakdown. In some cases it is desired to reduce particles to the point that they provide a stable suspension or emulsion. Such emulsions may become semi-transparent or translucent. Suspending agents or emulsification stabilizers may be employed. When cartilage is slow-frozen other reduction techniques are useful. These techniques can involve impacting equipment such as hammer mills or the like that use impact to reduce particle size. The size reduction technique can also involve the use of particles of cartilage impacting other cartilage particles at high speed and reduced temperature so as to cause breakage in a process that has been called "micronizing". Any of these size reduction processes may be carried out at a variety of reduced temperatures. Often it is convenient to use liquid nitrogen or dry ice to achieve these temperatures. Dry ice ($CO_2$) is preferred because it aids in the practice of this invention by, in addition to maintaining low temperature, providing a desired $CO_2$ atmosphere during size reduction. In any case it is necessary to control the temperature during grinding, since grinding processes generate heat. Since the collagen structure is changed (denatured) at elevated temperatures it is necessary to control temperatures during comminution. The exact relationship between temperature and time at that temperature is not known, but suitable conditions can be easily determined by those familiar with the art of size reduction and the denaturization of collagen. Many of the grinding processes mentioned in the literature, such as those used by Schilling (U.S. Pat. No. 7,083,820) must have instantaneous and localized high temperatures caused by impacts during grinding. Apparently this heat is applied for too short a time to have a great effect on denaturization of the type II collagen or the effect is too localized (small) to greatly reduce the amount of undenatured collagen. When dealing with bulk average temperatures the following preferences apply in the present invention. Temperatures approaching 210° F. cannot be tolerated, except perhaps for only an extremely short time, without denaturing the collagen and thus rendering it ineffective for amelioration of the symptoms of arthritis. Temperatures as high as 160° F. can be tolerated for slightly longer times. It is most preferred, however, to have bulk temperatures that do not exceed about 110° F. When temperatures are at this level or lower the cartilage or other biologically active, potentially useful substances will retain their undenatured structure for at least a matter of hours, which is more than enough time for any anticipated drying, size reduction, or other processing.

Drying at temperatures of 110° F. or below will in some cases be desirable in the practice of the present invention since some of the useful grinding techniques will be most successful on the more brittle, dried cartilage. Small amounts of anti-clumping agents such as lecithin or hydroxypropyl methylcellulose may be used during this drying stage. The process of drying before grinding provides an alternative to using very low temperature grinding to get the finest sizes that can be obtained by mechanical means. When drying at temperatures of 110° F. or below it may be desirable to use an antimicrobial agent such as ethylene oxide and/or an environment such as provided by UV light.

It will often be desirable to sort the particles. This sorting might be done during the size reduction stage where particles exit the grinding chamber only when they can pass through a desired screen size. Sorting can also be accomplished by many other techniques familiar to those knowledgeable in the classification art, such as screening, cyclones, settling, or separating in an upward flowing gas stream (preferably $CO_2$). This latter technique is often called elution. Alternately, the particles can be separated by weight, which will be more highly automated as new techniques are developed. Preferably these sorting operations are carried out in a nitrogen and most preferably a $CO_2$ atmosphere. In some cases a mixture of the two gases is preferred.

The larger particles might be selected to be the proper dose size for humans, equines, or canines so that one particle per day is taken for each subject. These particles are then stored in carbonated water until consumed. Further size reduction can then be obtained by the natural process of chewing.

Finer particles can be blended to produce a slurry or suspension with carbonated drinks. These drinks would be consumed completely if they contain a single dose. They can alternately be packaged as a concentrate containing a week or a month or more supply. In the case of the concentrate, after mild agitation to promote uniformity, a single dose can be metered out, for example, in a spoon or measuring cup. Special metering containers can also be used. For example, a metering chamber may be provided in a flexible bottle. Squeezing the bottle fills the metering chamber. The contents of the chamber can then be expelled as a therapeutic dose. The container can then be recapped. Such containers are well known in the art of metering gasoline additives, for example. Refrigeration at this point, while not always necessary, helps retain the $CO_2$ in the container for the relatively short storage period and is preferred.

The materials processed according to the present invention can be any organic substance that contains sufficient water causing it to be subject to deterioration as a result of the action of light, enzymes and pathogens, and spoilage organisms. Thus proteins, lipids, fats, and carbohydrates are included as well as any other water-containing biologically active substance. The materials processed according to the present invention typically require stabilization during processing, storage, handling and distribution, and consumption and/or use so that such deleterious effects do not occur. The materials are generally intended to be stored at room temperature, but can also often be refrigerated and/or properly frozen, although this is generally not necessary. There is no requirement to purify the organic substances in the present invention since the process of the present invention can be employed with mixtures of organic substances. The addition of other natural or synthetic substances, such as coloring agents and antioxidants, does not take such mixtures outside the scope of the present invention. However, the process of the present invention finds particular utility in conjunction with the processing of proteins where it is desirable to maintain the original undenatured structure of the proteins and food materials which contain combinations of proteins which have a synergistic effect when consumed. For example, chicken cartilage contains not only type II collagen but in addition contains such proteins as glucosamine and chondroitin. As disclosed in the aforementioned Moore patents (U.S. Pat. Nos. 5,645,581; 5,637,321; 5,529,786; and 5,750,144), the use of undenatured type II collagen reduces the symptoms of rheumatoid arthritis or other autoimmune types of arthritis which may in part be due to the nature of the undenatured type II collagen or the combination of such with other proteins present in chicken cartilage. In contrast, denatured, purified type II collagen does not provide the same type of relief or benefits as compared to the undenatured type II collagen.

EXAMPLES

Examples 1a and 1b, among other things, demonstrate the effectiveness of carbonated water to store cartilage for relatively short times if not pretreated to remove most pathogens, thereby pointing out the importance of pretreatment to remove or greatly reduce such pathogens as preferred in the present invention.

Example 1a

Chicken breasts are purchased from a local supermarket. The sternum cartilage is removed and stripped free of almost all visible flesh. The cartilage is refrigerated for 3 days then cut into small pieces. One gram is placed into each of four cleaned ordinary plastic carbonated beverage bottles. The cartilage receives no particular surface treatment, such as chlorine or $H_2O_2$, to destroy microorganisms. In order to test the ability of $CO_2$ to prevent spoilage, $CO_2$ in water is used at three levels. Standard Schweppes™ brand club soda is used containing about 0.6% $CO_2$ by weight and is chilled before being opened. Tap water that has been boiled and then chilled is used as the diluent. In Table 1, the High level is undiluted club soda water, Medium is 50% club soda water, Low is 25% club soda water, and Zero is pure boiled tap water.

Visual observations of the bottle contents are shown in Table 1. These observations clearly demonstrate the short-term preservative advantage of water containing $CO_2$ and the ability to retard the growth of microorganisms that still remain on the un-pretreated surface of the cartilage. The required long-term storage can only be obtained when most of the bacteria or other undesirable pathogens and other microorganisms are first destroyed by antimicrobials such as chlorine or $H_2O_2$. The term "long-term storage" is defined herein as 1 month or longer.

TABLE 1

Effect of $CO_2$ level on Untreated Cartilage Storage Stability

| Time | $CO_2$ Concentration | | | |
|---|---|---|---|---|
| (h) | High[a] | Medium[b] | Low[c] | Zero[d] |
| Start | clear | clear | clear | clear |
| 13 | clear | clear | clear | very slight haze |
| 62.5 | clear | very slight haze[e] | slight haze | cloudy |
| 132.5 | very slight haze | distinct haze | cloudy | cloudy with sides sucked in |

[a]Undiluted club soda water
[b]Club soda water diluted to 50%
[c]Club soda water diluted to 50%
[d]Pure boiled tap water
[e]Note that formation of a haze is a well-known indictation of undesireable microorganism growth.

Example 1b

This example, among other things, demonstrates that increased $CO_2$ content in the water increases storage time. Example 1a is repeated except pressurized $CO_2$ gas is added to the initial chilled club soda water, causing the amount of dissolved $CO_2$ to increase by a factor of about 1.5. A significant increase in storage time results without haze or other visible change being seen. It is anticipated that a higher level of $CO_2$ might be found that would perform the dual function of a) destroying pathogens and microorganisms, and b) preserving the effectiveness of the undenatured type II collagen in ameliorating the effects of arthritis. The present invention, however, requires in a preferred embodiment that a high degree of pathogen removal be carried out to a degree that will result in successful long-term storage as shown, for example, in Example 2 below.

Example 2

This example, among other things, demonstrates a preferred technique for removing surface contamination before storage. Chicken breasts are purchased from a local supermarket. The sternum cartilage is removed and stripped free of visible flesh. The cartilage is refrigerated then cut into small pieces as in Example 1. In this case the cartilage is treated with a common chlorine-releasing compound (such as NaOCl) before being cut up. The cartilage is drained, then exposed to 3% by weight $H_2O_2$ in water as described in Example 1 of U.S. Pat. No. 5,750,144. Two glass bottles of club soda (containing about 0.6% $CO_2$ by weight) are purchased. One-half gram is then placed into a bottle of chilled club soda and the bottle is tightly resealed. Another 0.5 gram is similarly placed into the second bottle that is now filled with water that has been boiled to kill any microorganisms, then chilled. These samples are then stored at ambient temperature for an extended period of time and observed periodically. Surprisingly, storage of cleaned cartilage in the carbonated water retains its original shape and coloration for more than 8 years, a much longer time than the untreated cartilage sample of Example 1. This is also very much longer than might be anticipated by anyone skilled in the art of using aqueous $CO_2$ in extending the useful life of food substances.

Example 2a

This example illustrates the surprising difference between the aqueous $CO_2$ product of the present invention and past art concerning the use of gaseous $CO_2$ in maintaining the usefulness of digestible substances. As shown in Table 2, the useful life of past art is measured in days while the product of the present invention is useful after more than 8 years.

TABLE 2

Performance of $CO_2$ in Maintaining Usefulness of Digestible Substances

| Time | Present Invention | Coyne[a] | Anzuetto[b] | Haines[c] | Ogilvy[d] |
|---|---|---|---|---|---|
| 8 years | useful | — | — | — | — |
| 6 years | useful | — | — | — | — |
| 4 years | useful | — | — | — | — |
| 2 years | useful | — | — | — | — |
| 12 months | useful | — | — | — | — |
| 6 months | useful | — | — | — | — |
| 3 months | useful | — | — | — | — |
| 26 days | useful | useful | — | — | — |
| 16 days | useful | useful | — | — | — |
| 6 days | useful | useful | useful | — | — |
| 76 hours | useful | useful | useful | useful | useful |

[a]Coyne studied the usefulness of 100% $CO_2$ compared to air in slowing the deterioration of a variety of fresh fish. (Effect of Carbon Dioxide on Bacterial Growth with Special Reference to the Preservation of Fish; *J. Soc. Chem. Ind*, 52, 1933, 19-24)
[b]Anzuetto demonstrated the usefulness of 30% $CO_2$ on retarding decay of strawberries; only 8.3% decay after 6 days while untreated experienced 64.4% decay. (Microatmosphere Packaging of Apples; *Inst. of Food Tech. Annual Meet.*; June 10-13, 1984)
[c]Haines studied the usefulness of 100% $CO_2$ compared to air in slowing the growth of *Pseudomonas*, *Proteus* and *Achromobacter*, chief constituents of the bacterial flora present on lean meat. (Influence of Carbon Dioxide on the Rate of Multiplication of Certain Bacteria as Judged by Viable Counts; *J. Soc. Chem. Ind.*, 52, 1933, 13T-17T)
[d]Ogilvy studied the effect of 25% $CO_2$ on prolonging the storage life of cut-up chicken. (Post-Mortem Changes in Meats II. The Effects of Atmospheres Containing Carbon Dioxide in Prolonging the Storage Life of Cut-up Chicken; *Food Technology*, 5, 1951, 97-102)

Example 3

This example, among other things, demonstrates the surprising retention of effectiveness of cartilage stored by the technique of this invention in ameliorating the effect of arthritis. It also shows that some patients require a larger dose to see the advantages of the present invention. A larger quantity of fresh sternum cartilage is obtained from a chicken processing facility and is prepared as in Example 2 and is cut into about 0.5 gram pieces. About a 1 month supply of cartilage is then packaged, sealed, and stored in each of many glass bottles, each with the concentration of $CO_2$ as in Example 2. They are stored for over 3 years at room temperature. These samples are used to demonstrate that, after long-term storage in aqueous $CO_2$, the cartilage retains its effectiveness.

After the storage period, the sample container is refrigerated to retard $CO_2$ loss and then opened each day to remove a sample for consumption and quickly resealed to retain the $CO_2$. The cartilage is consumed in daily doses according to the present invention by two females suffering from arthritis. The cartilage is consumed as relatively large pieces, often a single piece which is then chewed to reduce the particle size and allow it to be more easily absorbed. One of the two females finds reductions in the symptoms of arthritis in about a week and the reduction continues to increase most significantly over the first month with slower improvement continuing thereafter for many months. The second female sees little change at the lower dose but then sees a similar improvement when the dose is five times the lower dose. This demonstrates that some patients require a higher dose to trigger the oral tolerization process. The cartilage containing type II collagen, stored long term in aqueous $CO_2$, is surprisingly shown to have retained its effectiveness in ameliorating the effects of arthritis in humans.

Example 3a

This example, among other things, demonstrates that effectiveness remains after being stored in aqueous $CO_2$, then removed from the water containing $CO_2$ and stored for short terms at low temperature. Example 3 is repeated except, after opening a sealed glass bottle containing about a 1-month supply of cartilage, the cartilage particles are drained, put into a plastic bag, and slowly frozen and stored. A therapeutic amount of this cartilage is consumed each day by two other females with beneficial results.

Example 3b

This example, among other things, demonstrates the effectiveness of the product of the present invention in treating other species of warm-blooded animals. Example 3 is repeated except dogs are used. The amount of cartilage in each bottle is reduced. This reduction is to supply about the same cartilage-to-weight ratio as in the human example. For dogs, the stored cartilage is cut into small particles before consumption. A group of dogs suffering from osteoarthritis are given cartilage similarly to humans in Example 3 and similar beneficial results are seen.

Example 3b

This example, among other things, further demonstrates that storage of undenatured cartilage containing type II collagen in the presence of aqueous $CO_2$ is capable of maintaining or improving the effectiveness of that stored cartilage in ameliorating the symptoms of arthritis over long periods of time. As in Example 2, cartilage samples are stored for over 3 years in aqueous $CO_2$ at room temperature except the samples have had an additional 6 months of storage time in aqueous $CO_2$. A group of dogs suffering from osteoarthritis are given cartilage and similar, but slightly superior, beneficial results are seen. This example again indicates that long-term storage in aqueous $CO_2$ maintains or even improves the effectiveness in ameliorating the effects of arthritis.

Example 3c

This example, among other things, demonstrates the surprising ability of the product of the present invention to show a preventative effect when given to warm-blooded mammals before the occurrence of autoimmune arthritis, such as osteoarthritis. The procedure of Example 3b is repeated except a group of older dogs is chosen from a breed that is particularly susceptible to osteoarthritis but have not yet contracted it. The dogs are dosed as above over a period of 2 years. The incidence of osteoarthritis in this dosed group is compared to a matched group of dogs not dosed. The dosed dogs are found to have a very significant reduction in the incidence of osteoarthritis.

The result of this example demonstrates a surprising, and previously unknown, potential of the product of this invention to reduce the incidence of arthritis. This discovery has tremendous potential to reduce the incidence of arthritis in all warm-blooded mammals. The use of undenatured Type II collagen contained in chicken cartilage and many pharmaceuticals have shown an ability to reduce suffering from arthritis once it has begun its painful and devastating progress. However, the present invention is the first to surprisingly show the ability to reduce the inception of arthritis. The product of our invention appears to serve as an apparent "vaccine" against osteoarthritis.

Example 3c2

Figure 2:
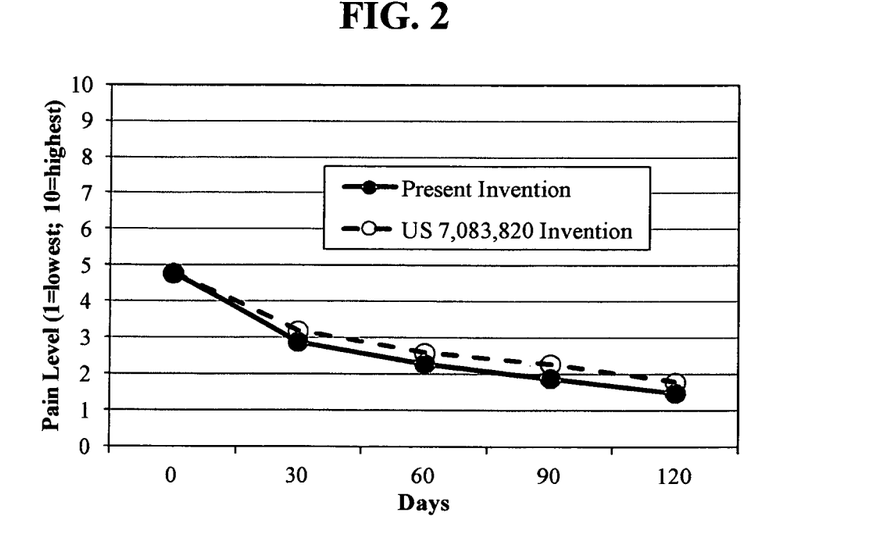
FIG. 2 shows the performance of chicken cartilage stored in aqueous $CO_2$ based on overall pain level for arthritic dogs.

This example further illustrates the improved effectiveness of the product of this invention compared to the product of the '820 patent in the treatment of dogs already afflicted with osteoarthritis. Twenty older dogs are selected that are already arthritic and overweight. These dogs are divided into two groups. Individuals in the first group are randomly selected and treated once a day with the product of the '820 patent containing 10 mg of undenatured type II collagen as dried product. The second group is fed an equivalent amount of type II collagen that had been stored in small glass bottles for over 1 year in the presence of aqueous $CO_2$. In all cases they are fed close to or during meal time. Overall pain is measured on a scale of 1 to 10 with 1 being no visible pain and 10 being severe and constant pain. A physical examination is performed once a month. The dogs are examined rising from a sitting and laying down position as well as laying down from a standing position. The results shown in FIG. 2 further illustrate the superior performance of the product of this invention and the benefits of the storage of chicken cartilage in carbonated water.

Example 3d

This example, among other things, demonstrates effectiveness of the product of the present invention with horses. It also shows that, after amelioration of the symptoms of arthritis, continued usage can surprisingly prevent reoccurrence. The procedure of Example 3 is repeated except a horse suffering from severe arthritis is dosed for several months with a similar cartilage-to-weight ratio, which is then varied to find a preferred dose. Significant improvement in the horse's symptoms is seen. When the administration of cartilage is stopped, the symptoms return within days. When administration of the aqueous $CO_2$ stored cartilage is resumed, the improvement resumes. In addition to demonstrating effectiveness with horses, this example demonstrates the ability to prevent reoccurrence. An additional advantage is seen in that wet product of the present invention adheres to the dry grain and is nearly completely consumed. In contrast, the dry product of the '820 invention tends to separate from the grain, settle to the bottom of the serving dish, and be refused by the horses. More than 10% is thus wasted.

Example 3e

This example, among other things, demonstrates the superiority of the product of this invention over the dried product of the prior art. This example also demonstrates the surprising effect that some mammals require a larger dose to activate the desired oral tolerization effect. In order to demonstrate the superior performance of the $CO_2$-stored cartilage a comparative example to the prior art of Schilling's U.S. Pat. No. 7,083,820 is arranged. The procedure of Example 3b is repeated and a matched group of dogs is chosen that have arthritis. The product of '820 is purchased from Swanson under the trade name of UCII. The UCII capsule, according to the label, contains 10 mg of undenatured type II collagen. When the matched group is dosed with an equivalent amount of the UCII, improvements in the arthritis symptoms in the dogs are seen. These improvements, however, are statistically seen to be significantly less than the improvements for the undenatured type II collagen of the present invention. Thus the superiority of the product of the present invention is further demonstrated.

Example 4

This example, among other things, demonstrates the effectiveness of a uniform slurry of the product of this invention. A quantity of fresh sternum cartilage is obtained from a chicken processing facility. The cartilage is stripped of adhering flesh. The cartilage is then treated at room temperature in a dilute solution of NaOCl (about 1.5% by weight) for about 20 minutes. The cartilage is drained, rinsed with carbonated water, and reduced in size with a slicing tool, producing finely sliced, then cross-sliced pieces. It is then placed into a container which contains 3% by weight stabilized $H_2O_2$ in water. After about 1 hour, the cartilage is drained to remove excess $H_2O_2$. Several bottles of club soda (containing about 0.6% $CO_2$ by weight) are purchased to store the sliced cartilage in an aqueous $CO_2$ environment. A small amount of the carbonated water is drained from each bottle and the drained cartilage is added to produce a slurry of about 10% by weight cartilage. The capped, cartilage-containing bottles are stored at room temperature until shortly before use, at which point they are refrigerated. Once a cooled container is opened for use, it is then continuously maintained cool in order to slow $CO_2$ loss. Before each use the container is mildly agitated to produce a uniform slurry, which is then poured to measure a uniform dose. This product is then shown to be effective in ameliorating the symptoms of arthritis.

Example 4a1

This example, among other things, demonstrates one of many alternate methods for the preparation of the product of the present invention in aqueous slurry form. Example 4 is repeated except the slurry is prepared in a common 6-cup food chopper/blender, RIVAL model TB-170 sold by Wal- Mart. As in Example 4, a quantity of fresh sternum cartilage is obtained from a chicken processing facility. The cartilage is stripped of adhering flesh. The cartilage is then treated at room temperature in a dilute solution of NaOCl (about 1.5% by weight) for about 20 minutes. The cartilage is drained, rinsed with carbonated water, and placed into a container which contains 3% by weight stabilized $H_2O_2$ in water. After about 1 hour the cartilage is drained to remove excess $H_2O_2$. Forty-three grams of clean cartilage is placed into the blender along with 391 grams of bottled soda water along with six ice cubes weighing about 17 grams each. The blender is operated for 6 minutes then half of the resulting slurry is placed into an ordinary kitchen carbonator and carbonated with a standard $CO_2$ capsule. The product is stored in a sealed bottle for about 6 months. This product is then shown to be effective in ameliorating the symptoms of arthritis.

Example 4a2

This example, among other things, demonstrates effective use of cartilage slurries at a higher solids level. Example 4a1 is repeated except at a higher solids level of about 20% by weight. In this case the $CO_2$ concentration is increased by about 20%. The product is similarly effective. The upper limit of solids will be apparent to those familiar with the art of liquid/solid slurries and will be affected by the particle size and shape. Suspending agents such as methylcellulose and the like will also have an effect on both the achievable solid content and settling rate.

Example 4a3

This example, among other things, demonstrates that it is unnecessary to remove attached tissue when the product is in slurry form. Example 4a1 is repeated except with "as received cartilage" that is not stripped of the attached tissue. In this sample, which appears to be typical, it is found that the cartilage contains 16.4% by weight of attached material. Other than a slight increase in slurry viscosity no difference in appearance is seen between the product of Example 4a1 and this product. The product is stored in a sealed bottle for about 6 months. This product is then shown to be effective in ameliorating the symptoms of arthritis.

Example 4a4

This example, among other things, demonstrates the value of the use of antifoam additive in preparation of the product of this invention in slurry form. Example 4a1 is repeated except immediately prior to use of the blender a small amount of food-grade silicone antifoam suspension is added. This addition is found to improve the process by reducing the time required for the foam to dissipate both during the blending and carbonation steps. There are many other compounds that might be used to reduce foam, which will be apparent to those skilled in the foam reduction art.

Example 4b

This example, among other things, demonstrates the beneficial effect of flavor-enhancing and/or pH-lowering additives. Example 4 is repeated except, in addition to the $CO_2$, a small amount of phosphoric acid is added in an amount to reduce the pH to about 3. The product is found to be similarly effective and has an improved flavor.

Example 5

This example, among other things, demonstrates the ability to effectively use a wide variety of water-based liquids in the practice of the present invention. It also demonstrates that larger doses are required for some mammals. Example 4 is repeated to prepare the finely sliced cartilage to the point that it is drained of excess $H_2O_2$. In a manner similar to Example 4, cartilage is placed into containers to produce a slurry with about 10% by weight solids. The containers are then filled with a wide variety of liquids that would normally be considered to be safe and pleasant to consume by humans. Other containers are then filled with a variety of sterile liquids that would normally be considered to be safe, promoting of improved health, and/or pleasant for canines or equines to consume. The contents of the containers are then carbonated with $CO_2$, using a common kitchen type carbonator with a small cartridge containing $CO_2$ to about the same level as for club soda (about 0.6% $CO_2$ by weight) or more. Other pressurization techniques well known in the carbonation of beverage art could be used with similar effect. After carbonation, the bottles are stored at ambient temperature until opened, after which refrigeration is preferred to help retain $CO_2$ for short-term storage periods. As in Example 4, the multiple products are shown to be effective in ameliorating the symptoms of arthritis.

Example 5a

It is found convenient to store multiple doses in a single bottle and to measure single doses from a gently agitated bottle. It is also found convenient to package a single dose per container, which can then be consumed completely. For some mammals it is found useful to consume larger quantities, or to consume the same quantity two or more times per day, or to consume larger initial doses (sometimes called loading doses), then to gradually reduce dose size until a level is found that is not effective. The dose is then increased back to the lowest previously demonstrated effective dose.

Example 6

This example, among other things, demonstrates the superior performance of the product of this invention compared to the product of prior art. In this example cartilage that has been prepared according to U.S. Pat. No. 7,083,820, which is assumed to have been dried in the presence of KCl, is purchased as UCII from Swanson. The finely ground cartilage is then soaked in club soda to remove the KCl and any other water-soluble materials. The cartilage is then filtered, washed with club soda, and resuspended in club soda. The cartilage is found to be effective in ameliorating the symptoms of arthritis. This product, however, is slightly less effective than the product of the present invention.

Example 7

This example, among other things, demonstrates the surprising usefulness of alternatives to the salt of '820 to maintain sterility during drying. This example produces a product that is as effective or only slightly less effective than the major product of this invention. Example 4 is repeated except after treating with $H_2O_2$, the cartilage is reduced in size and then dried at 110° F., and then reduced in size in an impact-type apparatus. Instead of using salts as in the '820 patent, a small amount of an antibacterial gas, chlorine in this case, is maintained in the recirculating air stream. In several steps, the amount of chlorine is increased until a level is found that prevents biological growth during drying in an equivalent manner to that of the salts of the '820 patent. In this case the warm air is cooled to condense and remove water, then reheated before being returned to the drying chamber. A make-up supply of chlorine is added to replace that amount removed with the condensed water. The resulting dried, then finely ground product is suspended and stored in carbonated water (water containing about 0.6% $CO_2$ by weight). After several months of storage the product is found to be as effective or nearly as effective in amelioration of the symptoms of arthritis as the nondried product and is found to produce a more uniform slurry and to settle more slowly.

Example 7a

This example, among other things, demonstrates other antibacterial gasses may be used in place of chlorine. Example 7 is repeated except chlorine is replaced with ethylene oxide as the antibacterial gas, with similar beneficial results. It is possible to operate with air as the drying medium and stay well below the explosive limit. To eliminate the possibility of accidentally exceeding the explosive limit, nitrogen is used with ethylene oxide in place of air for the first experiment. In a second experiment $CO_2$ replaces the nitrogen. As in Example 7, the resuspended in aqueous $CO_2$ product containing about 0.6% $CO_2$ by weight is found to be effective in ameliorating the symptoms of arthritis.

Example 7a1

Example 7a is repeated where ethylene oxide is utilized to provide an antimicrobial atmosphere to produce a dried, then finely ground product which is then packaged aseptically and found to be effective in ameliorating the symptoms of arthritis. Aseptic conditions are maintained, in this case, by using only pre-sterilized handling and packaging materials wherein a combination of heating to over 160° F., rinsing with isopropyl alcohol, and exposure to UV light is used. Packaging is carried out in a clean-room type environment. In this case, clean room air is recirculated past intense UV light which destroys virtually all microorganisms, then air is passed through a fine HEPA type filter which removes all microorganisms, both dead and those that might have escaped the UV light. Workers entering this clean room environment are required to shower and change clothes in an intermediate room. Disposable outer clothing, covering feet body and head, along with disposable gloves and filter masks covering the mouth and nose are used. Automation may be used later to minimize or eliminate the need for people to enter the clean packaging room.

Example 7b

This example, among other things, demonstrates the usefulness of $CO_2$ as a gas during drying. Example 7 is repeated except drying takes place in a $CO_2$ atmosphere with an effective amount of chlorine gas added. A lower level of chlorine is required than in Example 7. As in Example 7 the dried and finely ground product is resuspended in water containing 0.6% $CO_2$ by weight and found to be effective in ameliorating the effects of arthritis.

Example 7b2

This example, among other things, demonstrates the usefulness of $CO_2$ as a gas during drying. Example 7b is repeated where drying takes place in a $CO_2$ atmosphere with an effective amount of chlorine gas added. A lower level of chlorine is required than in Example 7. The process is conducted until the water content of the starting material is reduced to below about 4% by weight. The resulting dried, finely ground product is then aseptically packaged in small capsules suitable for retail sales. Fine grinding is carried out in the same gas mixture as used for drying. The capsules are stored for 6 months at a temperature of 110° F. to accelerate aging. After this storage time, several are opened and inspected. They are found to have maintained their original color and are found free of other pathogens. The product is then found to be effective in ameliorating the symptoms of arthritis.

Example 7c

This example, among other things, demonstrates the usefulness of UV light as an antibacterial agent during drying. Examples 7b and 7b2 are repeated except an effective amount of UV light is used as the antibacterial agent during drying and grinding. There are many ways to supply the effective amount of UV light regarding optimizing the wavelength and positioning that will be well known to those familiar with the art in these areas. The product is then found to be effective in ameliorating the symptoms of arthritis.

Example 8

This example, among other things, demonstrates the ability to grind cartilage that has been slow-frozen, then ground at very low temperature in the presence of dry ice or liquid nitrogen. Example 4 is repeated except the size reduction is carried out using slow-frozen cartilage prepared as in Example 15, in the presence of a small amount of dry ice which is slowly added to an impact-type apparatus. It is found that at the low temperature the cartilage is brittle enough to be easily ground. This procedure also allows temperature control, which further allows more rapid grinding without overheating. When the preferred $CO_2$ is used, this procedure has the added advantage of intimately exposing the new cartilage surface to the beneficial effect of $CO_2$. When suspended in aqueous $CO_2$ according to the present invention the product is found to produce a more stable slurry due to the finer particle size. The product is stored for over 1 year, then found effective in ameliorating the effect of arthritis.

Example 8a

Example 8 is repeated with slow-frozen cartilage except after grinding the product is dried, using a small amount of antibacterial gas as in Example 7, and the product is packaged under aseptic conditions using an antimicrobial atmosphere as in Example 7a2. Similar beneficial results are obtained in ameliorating the symptoms of arthritis.

Example 9

Example 8 and 8a are repeated except dry ice is replaced with a cooling quantity of liquid nitrogen. In some cases it is found desirable to add chlorine or another antibacterial gas to gain the antibacterial benefits during grinding.

Example 10a1

This example, among other things, demonstrates the ability to utilize relatively thin flexible plastic containers with good gas barrier properties to store the product of this invention. Example 4a1 is repeated except the container is changed. Instead of storing in a large rigid container, the cartilage in aqueous $CO_2$ is stored in a flexible plastic "pouch". Although any relatively nonpermeable flexible plastic will do, for the present invention a 4-mil vinyl chloride/vinylidene chloride copolymer, formerly sold under the trade name of Saran, is used. The container is filled in a $CO_2$ atmosphere, then placed in a pressure chamber at about 20 psig of $CO_2$ pressure where it is heat-sealed. The product is stored for over 1 year at room temperature then found effective in ameliorating the effect of arthritis. Part of that time the container is stored in a vessel pressurized with about 5 psig of $CO_2$ to prevent or reduce the loss of $CO_2$ through the plastic wall of the pouch.

Example 10a2

This example, among other things, demonstrates the usefulness of flexible packages with higher permeability when stored in an aqueous $CO_2$ atmosphere. Example 10a1 is repeated except a more permeable plastic is used for the individual packages. In this case a lightly plasticized polyvinyl chloride film is used. After filling the capsules are placed in a metal pressure vessel, which is then filled with 20 psig of $CO_2$ for long-term storage. It is found that after removal from the 20 psig atmosphere the individual packets retain their usefulness for many days at room temperature. This useful time is extended when the external $CO_2$ pressure is reduced by storing product under refrigeration. This process is most useful in cases requiring a large number of doses to be administered in a short period of time. This example uses a facility housing many equine mammals, horses in this case. Plastic vessels, particularly plasma-coated, and other vessel types known in the art may be substituted for the metal pressure vessel.

Example 10b

This example, among other things, demonstrates the ability to produce small, single-dose packages using the product of the present invention. The technique of Example 10a1 is used to produce small, single-dose packages. These packages are stored for over 1 year then are found effective in ameliorating the effect of arthritis. For part of this time the packages are stored in a pressure vessel with a $CO_2$ atmosphere.

Example 10c

This example, among other things, demonstrates the ability to produce many single-dose packages on a single sheet. The relatively thin flexible plastic with good gas barrier properties of Example 10a1 is used to produce single-dose packages with multiple doses on a single sheet. In the pharmaceutical area these are often called "bubble packs". In this case the single doses are separated by perforations that allow easy tearing for removal of a single dose or multiple single doses. It is desirable in some cases to have each removable segment imprinted with pertinent information such as the cartilage name, dose, and date. The product is then found to be effective in ameliorating the symptoms of arthritis.

Example 11

This example, among other things, demonstrates the ability to vacuum-thy the cartilage then grind. The cartilage is then either suspended in carbonated water or aseptically packaged and utilized in dry form. As in Example 4, a quantity of fresh sternum cartilage is obtained from a chicken processing facility. The cartilage is stripped of most adhering flesh. The cartilage is then treated at room temperature in a dilute solution of NaOCl (about 1.5% by weight) for 20 minutes or more, then placed into a container which contains 3% by weight stabilized $H_2O_2$ in water. After more than 1 hour, the cartilage is rinsed with carbonated water, then reduced in size. Size reduction is carried out after the cartilage is first slowly frozen by placing it in a chamber that is only slightly below the freezing point of the water contained in the cartilage to produce a similar result as in Example 15, then vacuum freeze-dried at a temperature slightly below 32° F. until the moisture content is low enough to facilitate grinding. The freeze-dried product is found to have a porous structure which surprisingly renders it much easier to grind. Depending on the grinding process, there is an optimum level of moisture. In this case the moisture is below about 5% by weight. The product is then finely ground, then suspended and stored in water containing 0.6% by weight $CO_2$. After several months of storage the product is found to be as effective or nearly as effective in amelioration of the symptoms of arthritis as the never-dried product. When the moisture content is varied upward and low-temperature grinding is used, it is possible to produce a finely ground product that has no detectable loss in undenatured type II collagen over a range of moisture content. Depending on the comminution process selected, an optimum level will be found by those familiar with the grinding art. A higher moisture content is generally preferred where possible since it is found to be more readily absorbed. As shown in Example 7 above, it is desirable to have an antimicrobial gas atmosphere present during grinding. Further drying in the presence of antimicrobial gases as in above examples is found useful for aseptically packaging of the dried powder and use of those packages to ameliorate the symptoms of arthritis.

Example 12

This example, among other things, demonstrates the ability of water-soluble thickening agents to slow the separation of cartilage solids and, when added at lower levels, to stabilize suspensions. Example 4 is repeated except a water-soluble thickening agent is added to the blend of $CO_2$ containing water and the cartilage. There is a wide variety of such useful thickening agents known to those skilled in the art. In this case methylcellulose is used to provide a medium viscosity slurry. The suspension is seen to retain its uniformity over a wider period of time than the product of Example 4 without the need to agitate as frequently, or to agitate at all. The thickened aqueous solution containing the cartilage and $CO_2$ is shown to retain its effectiveness in ameliorating the effects of arthritis in humans. When added at lower levels, the methylcellulose thickening agent is seen to improve the stability of the suspension with only a negligible or very small increase in viscosity. This suggests surface activity to cause particles in some way to repel each other.

Example 12a

This example, among other things, demonstrates the ability to add water-soluble polymers at higher levels to form nonseparating "slurries". It is found that it is possible to thicken the material to about the consistency of toothpaste and package into single dose pouches as in Example 10b. These pouches are found to be particularly desirable and effective in dosing horses as in Example 3d. It is further found possible to place the toothpaste consistency material into toothpaste type containers, expel a dose at a time, then recap as in typical toothpaste use. As shown in previous examples, various materials and storage conditions are useful.

Example 13

This example, among other things, demonstrates the use of a technique for dose metering from a larger reservoir of the product of the present invention. There are many ways to meter a dose known to those familiar with metering techniques and devices. A particularly desirable technique is to use an overflow device on a volumetric unit that is built into a container for a large number of doses. Such a device is fabricated using polyethylene terephthalate. Cartilage prepared as in Example 4 is stored for several months in this container in the presence of $CO_2$. The bottle is very gently agitated to promote uniformity before each use, then the sides are compressed to force a dose into the metering chamber. When the compression is released, the excess fluid overflows the metering chamber and returns to the reservoir in the body of the bottle. The bottle is refrigerated before the initial opening and then stored under refrigeration both to conserve the $CO_2$ atmosphere and to prevent expulsion of fluid from the metering tube. After consuming for about a month, an elderly man is found to have greatly reduced symptoms of osteoarthritis, demonstrating the effectiveness of the undenatured cartilage stored and dispensed in this manner. As in earlier examples, escape of $CO_2$ can be prevented by storing the entire containers under a few prig of $CO_2$.

Example 14

This example, among other things, demonstrates the surprising effect of storage temperature on useful storage life of the product of the present invention. A series of slurry samples is prepared using the procedure of Example 4a1. These samples are stored at a variety of temperatures for 12 months, then tested for effectiveness. It is surprising to note that lower storage temperatures are not as useful as ambient temperatures in maintaining effectiveness for ameliorating the effect of arthritis. It is found that temperatures of 60 to 90° F. are most effective while temperatures of 55 to 95° F. are useful. Temperatures as low as about 35° F. or above about 100° F. are found to be undesirable while temperatures of 35° F. to about 55° F. show less effectiveness. Normally lower storage temperatures would be expected to increase the retention of effectiveness of the undenatured cartilage. This surprising result of reduced effectiveness of material stored at lower temperature is completely unexpected. This unexpected behavior is not understood but perhaps it relates to the reduced partial pressure of the $CO_2$ at the lower temperatures. The reduction of effectiveness above about 100° F. is in line with expectations and these experiments simply help to define the limits of the present invention.

Example 15

This example demonstrates that rapid freezing of untreated cartilage denatures a significant portion of the cartilage while slow freezing does not. As in Example 3, a quantity of fresh sternum cartilage is obtained from a chicken processing facility. A sample is flash-frozen in seconds with extremely low temperature air using a technique that is common to processing chicken. Another sample is slow-frozen over a period of several days by placing it into a thick-walled, foamed polystyrene container which is then placed into a freezer where the temperature is −10° F. The fast-frozen sample and the slow-frozen sample are both subjected to a measure of the amount of undenatured cartilage remaining using the enzyme-linked immunosorbent assay (ELISA) technique with a special adaptation that has been developed to detect undenatured type II collagen. Surprisingly, the fast-frozen sample shows significant loss of the undenatured cartilage while the slow-frozen sample shows no significant reduction in undenatured cartilage. This totally unanticipated result allows freezing of the raw cartilage to be used to prepare the product of the present invention. The cartilage can then be stored in larger batches with obvious processing advantages. These advantages become even more apparent as consumer demand for this product increases to require large-scale manufacturing. One advantage is the ability to use freeze-drying under vacuum or low temperature grinding, where the cartilage becomes brittle. When an additional sample of cartilage is frozen over a period of several hours, undenatured cartilage is again shown to be essentially unchanged. Further simple variations will define the shortest freezing times that do not cause cartilage to be denatured. These times will vary with the conditions such as temperature, size of the freezing batch, other heat-transfer conditions, or for a continuous process. Persons familiar with the art of heat transfer will readily determine optimum conditions for a particular application. Perhaps the rapid expansion of water associated with rapid freezing breaks essential molecular bonds while slower freezing allows time for molecular structures to relax and reorient to avoid the breaks.

Example 16

This example, among other things, demonstrates the use of type II collagen contained in the vitreous humor of eyes to both ameliorate the effect of arthritis and to produce nearly transparent suspensions. Fresh porcine eyes are acquired from a pig slaughterhouse. These eyes are less than 36 hours postmortem and have been stored at 5° C. in a saline solution. They are obtained from 3- to 6-month-old Chester White pigs weighing from 50 to 100 kilograms. Vitreous humor is removed from the eye. After carefully removing a highly pigmented ring, the remaining vitreous humor is placed into a blender with aqueous $CO_2$ where the contents are blended for 6 minutes then additional $CO_2$ is added in the previously defined kitchen carbonator to a $CO_2$ concentration of about 0.6% by weight. The product is found to have a degree of transparency. Transparency is a very desirable feature for market appeal. After several months storage, the aqueous $CO_2$ product is used to treat arthritic dogs. After trials to determine an effective amount of the slurry, the product is found effective in ameliorating the effects of arthritis in these canines.

Example 17

This example demonstrates a difference in the vitreous humor quality and quantity, depending on the mammal species. Porcine eyes of Example 16 are compared to bovine eyes in Table 3.

TABLE 3

Comparison of Vitreous Humor of Porcine and Bovine Eyes

| Parameter | Porcine Eyes | Bovine Eyes |
|---|---|---|
| Initial solids (wt %) | 0.32 | 1.3-1.7 |
| Nonsoluble solids (wt %) | — | 0.95 |
| Vitreous humor (g) | 2.6 | 14.7 |
|  | 6.8 | 26 |

It is seen that porcine eyes are smaller and thus have much less vitreous humor than bovine eyes. It is likewise seen that the solids content is much lower. Since it is the solids that contain the type II collagen, it is seen that the quality is higher in the bovine eyes. Bovine eyes are preferred for the practice of the present invention.

Example 18

This example, among other things, demonstrates the relative ease of reducing the particle size of the collagen contained in vitreous humor. This is accomplished by first placing the vitreous humor from several bovine eyes into the blender used in Example 4a1. Chopping the vitreous humor, along with carbonated water and ice cubes in the blender, produces a uniform slurry of medium-sized particles of vitreous humor, which are then passed through a small diameter tube under high pressure, further reducing the particle size. By passing the slurry through successively smaller tubes under higher and higher pressure an extremely fine dispersion is produced. When a small amount of water-soluble polymer is added, methylcellulose in this case, stability of the suspension is increased. When the initial vitreous humor is dispersed in water it apparently matches the refractive index of the water and is invisible. When placed into carbonated water, however, the tissue slowly separates and becomes visible. Thus it is important to do the size reduction rapidly once introduced into the carbonated water.

Example 18a

The small diameter tube apparatus of Example 18 is used again and Example 4a1 is repeated except the chopper blender step is increased to about 20 minutes to produce a finer slurry. Although the slurry is finer it is very difficult to operate continuously since the larger particles continue to plug the small diameter tubes. Developing the 5,000 to 10,000 psi pressure required is also very difficult. Normally a piston pump is used, however, the larger particles foul the check valves, causing flow to stop or at best be intermittent. Gear pumps are not able to generate sufficient pressure. It may be possible to produce the desired small particles by employing many changes of tube size to find the size that will not plug and will still break down the larger particles. With the many attempts and re-handling of the product it is found almost impossible to produce a noncontaminated product even though the desired, near translucent particle size is obtained.

Example 18b

Example 4a1 is repeated except the time in the chopper/blender is increased to about 20 minutes, with sterile ice added when required for temperature control, to produce a much finer dispersion. This dispersion is further reduced in size using a variety of equipment that some call colloid mills. In each case the resulting very fine dispersion is carbonated and stored for about 6 months. One type of equipment used is a Jayco/Greaves GM Rotor Stator batch mixer sold by Jayco Incorporated. Another is an IKA Type MK 2000/4, which is sold by IKA Branches worldwide. This type uses a cone-shaped rotor and stator with three stages of increasingly fine serration or grooves. The stator can be infinitely adjusted to obtain the desired gap setting between the rotor and stator. A third is the Charlotte colloid mill (Model SD-2) where particle sizes between 3 and 5 microns are obtained. In this case a coarser feed stream is used with the chopper/blender being employed for only a few minutes, just enough to produce a pumpable slurry. Several passes are needed to produce the desired particle size. The number of passes required is found to depend on the clearance between the rotor and the stator. The combined nonaerating, hydraulic shear and centrifugal action of this apparatus yields a preferred performance. All three of these equipment examples are found to be relatively easy to operate. They are readily fed with either gear or centrifugal pumps or their own centrifugal type pumping action. It is easy to produce translucent particle sized samples and prevent contamination. These are just three of the many types of manufacturers of colloid mills that are available and known to those familiar with the colloid art. Each product from these various devices is shown to be effective in ameliorating the symptoms of arthritis.

Example 19

This example demonstrates, among other things, a technique for removing the "strongly pigmented circle" from the vitreous humor. This is removed by hand only with great difficulty and with a significant loss of vitreous humor when done at ambient temperature. This is because of the elusive nature of the "circle" that makes it difficult to capture and remove. This nature also makes it more difficult to maintain microbe-free conditions. It is found that the pigment removal operation is easy to perform on either frozen eyeballs or on the removed and frozen vitreous humor. Five bovine eyeballs are frozen slowly so as to not denature the collagen. They are then dissected free of surrounding tissue while still frozen. When this tissue is removed the pigment circle is visible and more easily removed. The cleaned vitreous humor is stored frozen until further processing is desired, then it is thawed and processed as in Example 18. It is found desirable, during thawing, to expose the vitreous humor to NaOCl and $H_2O_2$ in the manner of Example 2 to improve sterility.

Example 20

The pH to the closest 0.5 pH unit is determined for different concentrations of $CO_2$ in water with the following results (Table 4):

| Sample Number | $CO_2$ Concentration (wt %) | pH |
|---|---|---|
| 1 | 0.62 | 5.5 |
| 2 | 0.088 | 5.5 |
| 3 | 0.020 | 6.0 |
| 4 | 0.0083 | 6.0 |

Sample number 1 is commercial sparkling water. Samples 2, 3, and 4 are commercial sparkling water diluted with distilled water.

Example 21

This example demonstrates, among other things, the difference between the storage life required for a perishable product such as packaged animal flesh (Ogilvy, *Food Tech.*, 5, 1951, 97-102) or organs for transplant (Wikman-Coffelt, U.S. Pat. No. 5,066,578). It is shown that these two products have a very short storage life compared to the product of this invention which product thereof has the stable multiyear shelf life required for a marketable neutriceutical product. For all of the tests, fresh chicken sternal cartilage is obtained from a chicken processing facility. The cartilage is shipped overnight and is still surrounded with ice when utilized. While still cold, four pieces are prepared by the process of the present invention wherein they are stripped of most extra flesh, then placed in a 10-oz, cleaned, glass club soda bottle. Cleaning involves a full cycle in a kitchen dishwasher followed by rinsing both the cap and the bottle in 91% isopropyl alcohol, than allowing both cap and bottle to dry. The four pieces are placed in the now-sterile bottles, then tap water containing 5.1 gram/liter of 8.25% by weight NaOCl is added to the bottles to cover the cartilage for just over 20 minutes. The bottle is then rinsed with $H_2O_2$ for over 20 minutes. Finally the bottle is triple-rinsed with, then stored in, additive free carbonated water containing 0.62% by weight $CO_2$ with pH of 5.5.

Another sample is prepared by the process of Wikman-Coffelt wherein a solution containing sodium bicarbonate ($NaHCO_3$) is used to store transplant tissue. Four pieces of the cartilage are placed in a bottle cleaned as above, using clean rubber gloves. These pieces are then covered with a 25 millimolar solution of $NaHCO_3$. This solution is prepared by the addition of 2.1 grams of $NaHCO_3$ into 1 liter of additive-free distilled water. The $NaHCO_3$ is purchased from Fisher Scientific and is provided by Acros Organics as 99.5% purity, nitrogen flushed.

Another sample is prepared by the process of Ogilvy (*Food Tech.*, 5, 1951, 97-102). Four pieces of the cartilage are placed in each of a 1-gallon plastic container and in a 10-oz glass club soda bottle cleaned as above, using clean rubber gloves. Since Ogilvy uses a gas (containing 25% $CO_2$ and 75% $O_2$) two sizes of containers are used to see if the gas-to-cartilage ratio makes a major difference. A dip tube is used to purge the large container for 20 minutes while the smaller is purged for 5 minutes. The containers are then capped and stored at room temperature next to the aqueous $CO_2$ products of the present invention and the sample stored in the $NaHCO_3$ solution.

Initially all samples have a "sparkling clean" white appearance. After two days the product of the present invention has the initial sparkling clean appearance. The sample stored in $NaHCO_3$ is already very cloudy, indicating severe bacterial or other pathogen growth. The Ogilvy sample still has a clean appearance but with some bright red spots that appear to be well-oxygenated blood. After five days the product of the present invention still has the initial sparkling clean, white appearance. The sample stored in the $NaHCO_3$ solution is judged to be more cloudy and is now slightly tan in color, indicating further bacterial or other pathogen growth. The Ogilvy sample in the 10-oz bottle has lost its spotty red appearance and assumed a light tan appearance. The 1-gallon container sample has also lost the red spots and is noticeably darker than the 10-oz sample.

After 11 days the product of the present invention still has the initial sparkling clean, white appearance. The sample stored in the $NaHCO_3$ solution is now cloudy with a mud-like tan color, indicating further bacterial or other pathogen growth. The Ogilvy sample in the 10-oz bottle has a slightly darker tan appearance. The 1-gallon container sample also is noticeably even darker with a grey color appearing; both discolorations are indicative of bacterial or other pathogen growth.

In all of the above cases the product of the present invention still has the initial sparkling clean, white appearance. It has no indication of deterioration as shown by color or cloudiness to indicate any bacterial or other pathogen growth that would render it unsuitable for commercial consumption. The appearance is similar to an earlier example that shows this characteristic of the product of the present invention still existing after 8 years.

The sample stored in the $NaHCO_3$ solution shows signs of bacterial or other pathogen growth almost immediately. Storage in the $NaHCO_3$ solution appears to provide only short-term life support for a transplantable organ under the sterile conditions associated with organs removed under surgically clean conditions.

The cartilage stored in the carbonated water for 12 days is tested for biological contamination and has a total plate count of less than 10 colony forming units per gram (cfu/g) of cartilage, a total coliform count of less than 10 cfu/g, a yeast count of less than 10 cfu/g, a *Staphylococcus aureus* count of less than 10 cfu/g, a mold count of less than 10 cfu/g, and a *Pseudomonas aeruginosa* count of less than 10 cfu/g.

The cartilage stored in the $NaHCO_3$ solution for 12 days is tested for biological contamination and has a total plate count too numerous to count, a total coliform count of less than 10 cfu/g, a yeast count of 2,400 cfu/g, a *Staphylococcus aureus* count of less than 10 cfu/g, a mold count of 75 cfu/g, and a *Pseudomonas aeruginosa* count of less than 10 cfu/g.

The cartilage stored in the mixture of $O_2$ and $CO_2$ for 12 days is tested for biological contamination and has a total plate count too numerous to count, a total coliform count of less than 10 cfu/g, a yeast count too numerous to count, a *Staphylococcus aureus* count of less than 10 cfu/g, a mold count too numerous to count, and a *Pseudomonas aeruginosa* count of less than 10 cfu/g.

Example 22

Comminuted pineapple is treated with chlorine then stored for 6 months in aqueous $CO_2$ containing 0.6% by weight $CO_2$. The resulting slurry of pineapple is found to be free of pathogens and stable against enzyme degradation.

Example 23

Willow bark is comminuted and suspended in aqueous $CO_2$ containing 0.6% by weight $CO_2$ and stored for 6 months. The resulting product maintains the activity of the naturally occurring acetylsalicylic acid and combines such with the other beneficial ingredients contained in willow bark and can be available as an over-the-counter remedy.

Example 24

Foxglove leaves are comminuted, combined with an antimicrobial agent, drained, and stored in carbonated water containing 0.6% by weight $CO_2$ and stored for 6 months.

The resulting product is useful as a *digitalis* remedy and can be made available as a pharmaceutical.

Example 25

Rape seed is combined with an antimicrobial agent, and then comminuted, drained, and stored in carbonated water containing 0.6% by weight $CO_2$ and stored for 6 months. The resulting product is useful as an additive to foods to control cholesterol.

Example 26

Aloe leaves are combined with an antimicrobial agent, drained, comminuted, and stored in carbonated water containing 0.6% by weight $CO_2$ for 6 months. The resulting product can be used for internal applications to increase immune resistance and in topical applications to aid in the healing of wounds. As can be seen from this and the foregoing examples a variety of organic materials containing biologically active components can be stored in carbonated water without destroying the original structure of such components, thereby maintaining the efficacy of the active component. The foregoing examples are not to be construed as limiting the scope of this invention, which finds utility for products in pharmaceutical and medical fields, in dietary supplements, in herbal remedies sold over-the-counter, in the cosmetics industry, and in general food items which contain biologically active ingredients that are to be retained in their original natural state.

CONCLUSION

While the present invention has been described above according to its preferred embodiments, it can be modified within the spirit and scope of this disclosure. This patent application is therefore intended to cover any variations, uses, or adaptations of the present invention using the general principles disclosed herein. Further, the present application is intended to cover such departures from the present disclosure as come within the known or customary practice in the art to which this invention pertains.

What is claimed is:

1. A method for storing prepared chicken cartilage in an aqueous medium at room temperature without microbial spoilage of the prepared chicken cartilage, the method comprising the steps of: (a) separating chicken cartilage containing water-insoluble undenatured Type II collagen from chicken tissue to produce separated chicken cartilage; (b) sterilizing said separated chicken cartilage under conditions which do not change the original structure of the Type II collagen to produce a prepared chicken cartilage; (c) passing the prepared chicken cartilage through a rotating colloid mill to produce particles of the cartilage having a mean particle diameter of less than 10 micrometers; and (d) storing said particles of the cartilage having a mean particle diameter of less than 10 micrometers for more than six days but less than eight years at room temperature in an aqueous medium comprising more than 0.3 percent carbon dioxide by weight without microbial spoilage of the prepared chicken cartilage.

* * * * *